United States Patent [19]

Gramlich et al.

[11] Patent Number: 4,751,214

[45] Date of Patent: Jun. 14, 1988

[54] USE OF 2-TERT-BUTYL-4-METHYLCYCLOHEX-ANOL AS A SCENT AND AS A COMPONENT OF SCENT COMPOSITIONS

[75] Inventors: Walter Gramlich, Edingen-Neckarhausen, Fed. Rep. of Germany; Werner Hoffmann, New York, N.Y.; Klaas Jansen, Ludwigshafen, Fed. Rep. of Germany; Wolfgang Lengsfeld; Ludwig Schuster, both of Limburgerhof, Fed. Rep. of Germany

[73] Assignee: BASF Aktiengesellschaft, Rheinland-Pfalz, Fed. Rep. of Germany

[21] Appl. No.: 82,210

[22] Filed: Aug. 6, 1987

[30] Foreign Application Priority Data

Aug. 30, 1986 [DE]  Fed. Rep. of Germany ....... 3629605

[51] Int. Cl.$^4$ .................................................. A61K 7/49
[52] U.S. Cl. ..................................... 512/23; 568/834; 568/835; 512/22
[58] Field of Search ................... 512/22, 23; 568/834, 568/835

[56] References Cited

U.S. PATENT DOCUMENTS

| | | | |
|---|---|---|---|
| 2,574,077 | 11/1951 | Whitaker et al. | 568/834 |
| 4,343,955 | 8/1982 | Oshima et al. | 568/834 |
| 4,551,564 | 11/1985 | Otte et al. | 568/834 |
| 4,617,145 | 10/1986 | Schreiber et al. | 568/834 |

FOREIGN PATENT DOCUMENTS

| | | | |
|---|---|---|---|
| 2253849 | 5/1974 | Fed. Rep. of Germany | 568/834 |
| 2334928 | 1/1975 | Fed. Rep. of Germany | 568/834 |

*Primary Examiner*—Werren B. Lone
*Attorney, Agent, or Firm*—Oblon, Fisher, Spivak, McClelland & Maier

[57] ABSTRACT

2-tert-butyl-4-methylcyclohexanol is used as a scent and as a component of scent compositions.

Scent compositions contain 2-tert-butyl-4-methylcyclohexanol (I), which influences their fragrance. It has a very intense earthy woody vetiver-like fragrance and is stable in neutral, acidic and alkaline solutions.

2 Claims, No Drawings

USE OF 2-TERT-BUTYL-4-METHYLCYCLOHEXANOL AS A SCENT AND AS A COMPONENT OF SCENT COMPOSITIONS

In the area of perfumery and the development of aromas, in spite of the large number of known natural and synthetic scents, there continues to be considerable demand for novel scents which either have fragrance notes unknown to date or are capable of replacing scents which are expensive or difficult to obtain. The reason for this is the steadily growing demand for perfume compositions, both for fine perfumery and for cosmetic and industrial products, such as detergents, softeners and the like.

We have found that 2-tert-butyl-4-methylcyclohexanol (I) is a very interesting, versatile scent which is particularly useful in acidic and well as alkaline media and has an earthy woody vetiver-like fragrance, which furthermore is very intense.

I and its synthesis have been described by H. Ungnade and A. D. McLaren in J. Amer. Chem. Soc. 66 (1944), 118-124, in an article on the catalytic hydrogenation of phenols. However, the authors give no information about the interesting fragrance properties of this compound. Furthermore, there is no known description of I.

I is obtained in a simple manner by hydrogenating the corresponding phenol.

Hydrogenation of the nucleus of phenols is carried out in a conventional manner in the presence of a known hydrogenation catalyst, such as Raney nickel or a palladium, rhodium or ruthenium catalyst.

In the publication cited, Raney nickel was used as the catalyst. We obtained the best yields with ruthenium catalysts.

Depending on the reaction conditions used, various diastereomer mixtures were obtained, all of which however have interesting olfactory properties.

If hydrogenation is carried out in the presence of ruthenium, for example under a hydrogen pressure of 50 bar and at 120° C., the isomers shown in the scheme below are obtained in a isomer ratio of A:B:C:D=68:29:2:1. If hydrogenation is effected under a hydrogen pressure of 50 bar and at 200° C., the ratio A:B:C:D is 52:24:16:8. The isomer ratios were determined in each case by NMR spectroscopy ($^1$H and $^{13}$C NMR spectra).

Scheme

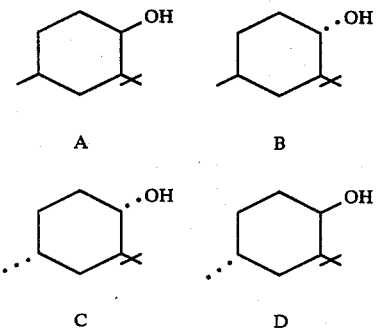

The diastereomer mixture of I obtained in this manner is a colorless liquid having an earthy woody vetiver-like fragrance.

Structurally related compounds which are already used in the scent sector are (1) d,l-menthol and (2) 2-tert-butylcyclohexanol:

(1) d,l-methanol (2-isopropyl-5-methylcyclohexanol), of which it is possible to distinguish four different d,l pairs, ie.
(a) d,l-menthol, in which all three substituents are in the equitorial position,
(b) d,l-neomenthol, in which only the hydroxyl group is in the axial position,
(c) d,l-isomenthol, in which only the methyl group is in the axial position and
(d) d,l-neoisomenthol, in which the hydroxyl group and methyl group are in the axial position.

Of the four racemates, d- and l-menthol are by far the most important ones commercially.

There are extreme differences between the ol-factory and organoleptic properties of d- and l-menthol. While the l-isomer has a fresh fragrance reminiscent of peppermint, d-menthol has a wood camphor note.

(2) 2-tert-butylcyclohexanol has a strong, camphor-like minty note.

It is therefore surprising that I has a completely different note.

Of particular importance is the fact that I has an intense fragrance and, even in very small doses, therefore introduces a clear accentuation, expression and radiance into compositions having a woody note.

According to the invention, it is possible to use individual diastereomers and diastereomer mixtures, as obtained in the hydrogenation described.

Its excellent stability in acidic, neutral and alkaline media opens up a wide range of applications for the novel scent.

I can very readily be combined with the conventional perfume ingredients and other scents to give novel compositions; the content in the scent compositions is in general from 0.1 to 50% by weight. Compositions of this type can be used for perfuming cosmetic preparations, such as creams, lotions, scents, aerosols, toilet soaps and oral hygiene agents, for hair cosmetics and in extract perfumery. They can also be employed for improving the odor of industrial products, such as detergents, cleaning agents and softeners.

The novel scent can be used individually and, in particular, as a mixture with other scents.

A preparation process, an example of use and a stability test are described below to illustrate the invention.

EXAMPLE 1

Preparation of 2-tert-butyl-4-methylcyclohexanol

A mixture of 400 g (2.44 moles) of 2-tert-butyl-4-methylphenol, 400 ml of dioxane and 1 g of ruthenium hydroxide was initially taken in an autoclave and hydrogenated at 120° C. and under a hydrogen pressure of 50 bar until the pressure remained constant (total hydrogenation time about 3½ hours). The catalyst was separated off, after which the dioxane was distilled off and the residue fractionated under 0.01 mbar. After a small initial fraction (15 g of a fraction having a boiling point up to 60° C./0.01 mbar), 401 g (2.36 moles, corresponding to a yield of 96% of theory) of 2-tert-butyl-4-methylcyclohexanol distilled over at 80°-85° C./0.01 mbar and, after cooling, solidified to a semisolid mass. On the basis of $^{13}$C NMR spectroscopic data, it was identified as a diastereomer mixture having the following composition:
A:B:C:D = 68:29:2:1.

Scheme

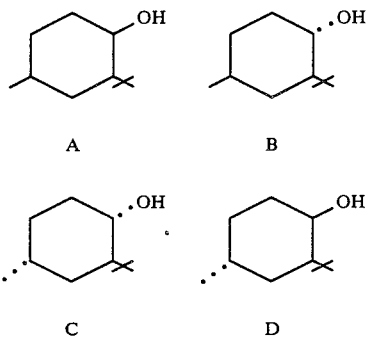

The diastereomer mixture ($n_D^{25}$ 1.4679) had a very interesting intense earthy woody vetiver note.

Depending on the reaction temperature and hydrogen pressures used, various diastereomer ratios of A, B, C and D are obtained, as illustrated in the Table below.

TABLE

| Example | Temperature [°C.] | Hydrogen pressure [bar] | Diastereomer ratio A: | B: | C: | D |
|---|---|---|---|---|---|---|
| 1 a | 120 | 50 | 68 | 29 | 2 | 1 |
| 1 b | 160 | 50 | 61 | 28 | 9 | 2 |
| 1 c | 180 | 50 | 58 | 23 | 14 | 5 |
| 1 d | 200 | 50 | 53 | 24 | 16 | 7 |

EXAMPLE 2

Use of I for rounding off a scent composition
Perfume oil (chypre type):

| Components | Content [parts by wt.] a | b |
|---|---|---|
| Citronellol | 40 | 40 |
| Dihydrorose oxide | 10 | 10 |
| Phenylethyl acetate | 20 | 20 |
| Isoeugenol | 5 | 5 |
| Coumarin | 15 | 15 |
| Bergamot oil | 80 | 80 |
| Fixolide ® NP | 25 | 25 |
| Pentylcyclopentanone | 5 | 5 |
| Hedione ® | 20 | 20 |
| Benzyl acetate | 40 | 40 |
| C 10 aldehyde 10% | 10 | 10 |
| C 11 (undecylene) aldehyde 10% | 20 | 20 |
| gamma-Methylionone | 80 | 80 |
| Vetiveryl acetate | 50 | 50 |
| Ambrox 10% in DEP | 5 | 5 |
| Jasmorange*/anthranilate | 10 | 10 |
| Styrallyl acetate | 10 | 10 |
| Phenylacetaldehyde dimethyl acetal | 10 | 10 |
| Tetrahydrolinalool | 40 | 40 |
| Hydroxycitronellal | 40 | 40 |
| Ylang ® Ylang oil | 5 | 5 |
| Petitgrain oil | 30 | 30 |
| Labdanym res | 10 | 10 |
| Mousse de Chene abs. | 25 | 25 |
| Patchouli oil | 30 | 30 |
| Linalyl acetate | 50 | 50 |
| C 14 aldehyde 10% | 30 | 30 |
| Dimethylbenzylcarbinyl acetate | 10 | 10 |
| Phenylethyl alcohol extra | 100 | 100 |
| Sandelether* | 40 | 40 |
| DPG ® | 135 | 95 |
| 2-tert-butyl-4-methylcyclohexanol | — | 40 |
| | 1,000 | 1,000 |

*Trade mark applied for

The perfume oil of composition a is a chypre complex having a pronounced vetiver note. If, instead of 40 parts of DPG ®, 40 parts (4% by weight) of 2-tert-butyl-4-methylcyclohexanol are added to complex a, the whole composition has a more intense effect; the woody complex is clearly accentuated, the vetiver note is emphasized and the composition is pleasantly rounded off and has more character and body.

EXAMPLE 3

Stability test 2-tert-butyl-4-methylcyclohexanol was stored for 30 days in acidic, neutral and basic media at 40° C. For this purpose, 0.5% strength by weight solutions of 2-tert-butyl-4-methylcyclohexanol in 60% strength by weight aqueous ethanol were prepared in each case, some of these solutions being brought to pH 1.7 with 1N HCl and others being brought to pH 14 with 1N NaOH. Under the above-mentioned conditions, I was shown to be stable in all test solutions by thin layer chromatography. Furthermore, no color or fragrance changes were detectable.

We claim:

1. A scent composition which contains 2-tert-butyl-4-methylcyclohexanol.

2. A scent composition as claimed in claim 1, which contains 2-tert-butyl-4-methylcyclohexanol in an amount of from 0.1 to 50% by weight, based on the total composition.

* * * * *